(12) United States Patent
Lewis et al.

(10) Patent No.: US 6,706,289 B2
(45) Date of Patent: Mar. 16, 2004

(54) METHODS AND COMPOSITIONS FOR ENHANCED DELIVERY OF BIOACTIVE MOLECULES

(75) Inventors: Danny Lewis, Hartselle, AL (US); Paul Schmidt, Niwot, CO (US); Kenneth Hinds, Fort Collins, CO (US)

(73) Assignee: PR Pharmaceuticals, Inc., Fort Collins, CO (US)

( * ) Notice: Subject to any disclaimer, the term of this patent is extended or adjusted under 35 U.S.C. 154(b) by 0 days.

(21) Appl. No.: 09/999,820

(22) Filed: Oct. 31, 2001

(65) Prior Publication Data

US 2002/0155158 A1 Oct. 24, 2002

Related U.S. Application Data

(60) Provisional application No. 60/244,499, filed on Oct. 31, 2000.

(51) Int. Cl.$^7$ ............................ A61F 2/02; A61K 47/30; A61K 9/50
(52) U.S. Cl. ..................... 424/501; 424/423; 424/489; 424/502; 514/772.3
(58) Field of Search ................................ 424/423, 489, 424/501, 502; 514/772.3

(56) References Cited

U.S. PATENT DOCUMENTS

| | | | |
|---|---|---|---|
| 4,179,337 A | 12/1979 | Davis et al. | ................ 435/181 |
| 5,102,872 A | 4/1992 | Singh et al. | ................... 514/21 |
| 5,320,840 A | 6/1994 | Camble et al. | ............ 424/85.1 |
| 5,446,090 A | 8/1995 | Harris | ........................ 525/54.1 |
| 5,672,662 A | 9/1997 | Harris et al. | ................ 525/408 |
| 5,880,255 A | 3/1999 | Delgado et al. | ............ 530/303 |
| 5,942,253 A | 8/1999 | Gombotz et al. | ........... 424/501 |

FOREIGN PATENT DOCUMENTS

| | | | |
|---|---|---|---|
| WO | WO 98/46212 A1 | | 10/1998 |
| WO | WO98/46212 | * | 10/1998 |
| WO | WO 02/41829 A2 A3 | | 5/2002 |

OTHER PUBLICATIONS

Bently, et al. "PEG Biphalin: A Potent Long–Acting Analgesic" *Proceed. Int'l. Symp. Control. Rel. Bioact. Mater.*, 28:1287–1288 (2001).

Hora, et al. "Controlled Release of Interleukin–2 from Biodegradable Microspheres" *Bio/Technology* 8: 755–758 (Aug. 1990).

Hora, et al. "Development of a Controlled Release Microsphere Formulation of Interleukin–2" *Proceed. Intern. Symp. Control. Rel. Bioact. Mater.* 16:509–510 (1989).

Katre, et al. "Chemimcal Modification of Recombinant Interleukin 2 by Polyethylene Glycol Increases its Potency in the Murine Meth A Sarcoma Model" *Proc. Natl. Acad. Sci. USA* 84:1487–1491 (1987).

Katre, et al. "Immunogenicity of Recombinant IL–2 Modified by Covalent Attachment of Polyethylene Glycol" *J. Immunol.* 144:209–213 (1990).

Misicka, et al. "Structure–Activity Relationship of Biphalin. The Synthesis and Biological Activities of New Analogues with Modifications in Positions 3 and 4." *Life Sciences* 60(15):1263–1269 (1997).

Yip, et al. "Direct Force Measurements of Insulin Monomer—Monomer Interactions" *Biochemistry* 37 (16):5439–5449 (1998).

* cited by examiner

*Primary Examiner*—Carlos A. Azpuru
(74) *Attorney, Agent, or Firm*—Lahive & Cockfield, LLP; Jane E. Remillard, Esq.; Hathaway Pease Russell, Esq.

(57) ABSTRACT

Formulations for controlled, prolonged release of bioactive molecules such as therapeutic proteins, peptides and oligonucleotides have been developed. These formulations are based on solid microparticles or nanoparticles formed of the combination of biodegradable, synthetic polymers such as poly(lactic acid) (PLA), poly(glycolic acid) (PGA), and copolymers thereof. Bioactive molecules are coupled to hydrophilic polymers such as polyethylene glycol or polypropylene glycol and formulated to provide controlled release. The bioactive molecules are more stable, less immunogenic and have improved release rate profiles with lower burst levels and increased drug loading relative to the same bioactive molecules lacking coupled hydrophilic polymers. The controlled release formulations can be administered by injection, by inhalation, nasally, or orally.

39 Claims, No Drawings

METHODS AND COMPOSITIONS FOR ENHANCED DELIVERY OF BIOACTIVE MOLECULES

RELATED APPLICATIONS

This application claims priority to U.S. Provisional Application No. 60/244,499 entitled "Methods and Compositions for Enhanced Delivery of Bioactive Molecules" filed on Oct. 31, 2000, the contents of which are incorporated herein by reference.

BACKGROUND OF THE INVENTION

Encapsulation of pharmaceuticals in biodegradable polymer microspheres and nanospheres can prolong the maintenance of therapeutic drug levels relative to administration of the drug itself. Sustained release may be extended up to several months depending on the formulation and the active molecule encapsulated. However many bioactive molecules, and especially proteins, are damaged or made unstable by the procedures required to encapsulate them in the polymeric carriers. Furthermore, the charged, polar nature of many proteins may limit the extent of encapsulation in polymer drug carriers and may lead to rapid loss of a fraction of the encapsulated bioactive molecule when first administered ("burst").

Encapsulation of bioactive molecules in biodegradable polymer delivery systems has been used to stimulate an immune response when administered to a patient (see U.S. Pat. No. 5,942,253 to Gombotz et al.). While this is a desired result in certain cases, it is undesirable when the purpose is delivery of the bioactive molecule for therapeutic purposes. Thus, diminished recognition by the immune system of bioactive molecules delivered using biodegradable polymers would be beneficial in a therapeutic setting.

Bioactive molecules, especially therapeutic proteins (drugs), may be modified with hydrophilic polymers (a process generally known as "pegylation"), such as polyethylene glycol, covalently attached to one or more amino acid side chains (see e.g., U.S. Pat. No. 4,179,337 to Davis et al.; U.S. Pat. No. 5,446,090 to Harris; U.S. Pat. No. 5,880,255 to Delgado et al.). While it is known in the art that such attachment may lead to an apparent increase in molecular mass and decreased blood clearance rate for the modified therapeutic protein (see e.g., U.S. Pat. No. 5,320,840 to Camble et al.), the prior art does not teach that diminished immunogenicity can be achieved or that the duration of release from biodegradable polymer drug delivery systems can be extended using pegylated proteins. The prior art does not teach that pegylation can increase the drug loading achievable in a biodegradable drug delivery system relative to the unpegylated drug, nor does it teach that reduced burst of drug is achievable for the pegylated moiety relative to the unpegylated drug.

SUMMARY OF THE INVENTION

The present invention provides novel formulations for controlled, prolonged release of bioactive molecules such as therapeutic proteins, peptides and oligonucleotides. The formulations are based on microparticles or nanoparticles formed of the combination of biodegradable, polymers such as poly(lactic acid) (PLA), poly(glycolic acid) (PGA), and copolymers thereof. Bioactive molecules are coupled to hydrophilic polymers such as polyethylene glycol or polypropylene glycol and then formulated with the solid microparticles or nanoparticles to provide controlled release. The controlled release formulations can be administered by injection, by inhalation, nasally, or orally.

Accordingly, as part of the present invention, it has been discovered that attachment of hydrophilic polymers to bioactive molecules, such as drugs and therapeutic proteins, has several beneficial effects, including providing protection from degradation and denaturation under the conditions of encapsulation in drug carriers. Additionally the amount of modified protein that can be encapsulated is increased relative to the unmodified protein, thus providing a lower total dose of material, benefiting both the patient and producer.

In addition, the present invention is further based on the discovery that immunogenicity of peglyated bioactive molecules encapsulated in biodegradable polymer drug delivery carriers is decreased relative to non-peglyated bioactive molecules in the carriers, particularly when administered by subcutaneous or intramuscular injection or inhalation or mucosal delivery (e.g., oral or nasal delivery). Such diminished immunogenicity is particularly advantageous when biodegradable polymers are used for oral delivery, since this is a typical method for mucosal vaccination.

In another aspect, the present invention is based on the discovery that pegylated proteins, peptides, oligosaccharides and oligonucleotides, which normally are not absorbed from the gastro-intestinal tract, are made bioavailable by administration in biodegradable polymer systems, particularly nanospheres. The term "bioavailable", as used herein, refers to the fraction of bioactive molecule that enters the blood stream following administration to a subject. The controlled release formulations of the invention increase the bioavailability of bioactive molecules and, in particular, the nanosphere formulations described herein when administered orally. For example, blood levels can be maintained for up to several days following a single oral administration of nanosphere encapsulated peglyated bioactive molecule. Additionally the polyethylene glycol chains protect the bioactive molecules from degradation and denaturation in the process of forming the nanospheres, contribute to increased entrapment of active material, and diminish the "burst" effect.

Thus, in a preferred embodiment, the invention provides a pharmaceutical composition for controlled, sustained release and increased bioavailability of a bioactive molecule, which includes a polymer (e.g., PEG) conjugated therapeutic agent encapsulated into nanospheres. In a particularly preferred embodiment, the composition is administered orally.

In a preferred embodiment, the bioactive molecule is selected from the group consisting of α-interferon, β-interferon, γ-interferon, erythropoietins, granulocyte colony stimulating factor, granulocyte macrophage colony stimulating factor, interleukin 1, interleukin 2, interleukin 3, interleukin 12, asparaginase, adenosine deaminase, insulin, ACTH, glucagon, somatostatin, somatotropin, thymosin, parathyroid hormone, pigmentary hormones, somatomedin, leuteinizing hormone, chorionic gonadotropin, hypothalmic releasing factors, antidiuretic hormones, thyroid stimulating hormone, endorphins, enkephalins, biphalin, prolactin, monoclonal antibodies, polyclonal antibodies, antisense oligonucleotides, aptamers, therapeutic genes, heparin, low molecular weight heparin and small bioactive molecules.

Accordingly, the compositions of the present invention can be used to improve in vivo delivery of therapeutic bioactive molecules in several respects. In particular, the invention provides the advantages of reduced immunogenicity, increased bioavailability, increased duration, increased stability, decreased burst and controlled, sustained release of bioactive molecules in vivo.

DETAILED DESCRIPTION OF THE INVENTION

I. Bioactive Molecules

The term "bioactive molecule", as used herein, refers to any therapeutic protein, peptide, polysaccharide, nucleic acid or other biologically active compound for administration to a subject, such as a human or other mammal. Suitable therapeutic proteins for use in the invention include, but are not limited to, interferon-alphas, interferon-betas, interferon-gamma, erythropoetins, granulocyte colony stimulating factor, granulocyte macrophage colony stimulating factor (GM-CSF), interleukin 1, interleukin 2, interleukin 3, interleukin 12, asparaginase, adenosine deaminase and insulin.

Suitable therapeutic peptides also include hormones, such as ACTH, glucagon, somatostatin, somatotropin, thymosin, parathyroid hormone, pigmentary hormones, somatomedin, luteinizing hormone, chorionic gonadotropin, hypothalmic releasing factors, antidiuretic hormones, thyroid stimulating hormone, endorphins, enkephalins, biphalin and prolactin.

Additional suitable therapeutic proteins include monoclonal and polyclonal antibodies, single-chain antibodies, other antibody fragments, analogs and derivatives. Therapeutic polynucleotides, including antisense oligonucleotides, aptamers and therapeutic genes also can be delivered using the methods and compositions of the invention.

Anticoagulant therapeutics, such as heparin and low molecular weight heparin, also can be delivered using the methods and compositions of the invention. Other suitable therapeutic proteins for the use in the invention include small bioactive molecules, such as anticancer drugs, e.g., paclitaxel, taxotere, doxorubicin and daunorubicin, vincristine, cisplatin, carboplatin, camptothecin and camptothecin analogs, antibiotics, antipsychotics, antidepressants, small molecule drugs for diabetes and cardiovascular disease.

II. Conjugation of Bioactive Molecules to Hydrophilic Polymers

The term "hydrophilic polymer" refers to any water-soluble linear or branched polymer including, but not limited to, polyethylene glycol and polypropylene glycol and similar linear and branched polymers. Preferably, the molecular weight of the polymer ranges from about 500 daltons to about 50,000 daltons. Hydrophilic polymers for use in the invention typically have a reactive group incorporated for attachment to the bioactive molecule of interest through amino, carboxyl, sulfhydryl, phosphate or hydroxyl functions.

Hydrophilic polymers used in the present invention, such as polyethylene glycol, can be prepared according to standard protocols with one end capped as with a methoxy group and the other end activated for facile conjugation to active groups on bioactive molecules. For example, U.S. Pat. No. 6,113,906 describes the use of succinamidyl succinate or carbamate reactive groups on the polyethylene glycol to react with amine groups on proteins. U.S. Pat. No. 5,446,090 describes the use of sulfone derivatives of polyethylene glycol to form stable bonds with sulfhydryl groups of proteins. U.S. Pat. No. 5,880,255 describes the use of tresyl derivatives for reaction at amine groups of proteins to form a simple, stable secondary amine linkage. The entire contents of these patents is incorporated by reference herein. N-hydroxy succinamide also may be incorporated as the reactive group.

III. Controlled Release Formulations for Polymer Conjugated Bioactive Molecules The term "controlled release" refers to control of the rate and/or quantity of bioactive molecules delivered according to the drug delivery formulations of the invention. The controlled release can be continuous or discontinuous, and/or linear or non-linear. This can be accomplished using one or more types of polymer compositions, drug loadings, inclusion of excipients or degradation enhancers, or other modifiers, administered alone, in combination or sequentially to produce the desired effect.

Zero order or linear release is generally construed to mean that the amount of the bioactive molecule released over time remains relatively constant as a function of amount/unit time during the desired time frame. Multi-phasic is generally construed to mean that release occurs in more than one "burst".

A. Microparticles

In one embodiment, the invention employs biodegradable microparticles for controlled release of polymer conjugated bioactive molecules. As used herein, "microparticles" refers to particles having a diameter of preferably less than 1.0 mm, and more preferably between 1.0 and 100.0 microns. Microparticles include microspheres, which are typically solid spherical microparticles. Microparticles also include microcapsules, which are spherical microparticles typically having a core of a different polymer, drug, or composition.

Microparticles for use in the present invention can be made using a variety of biodegradable polymers used for controlled release formulations, as are well known in the art. Suitable polymers for example include, but are not limited to, poly(hydroxy acids) including polylactic acid, polyglycolic acid, and copolymers thereof, polyanhydrides, polyorthoesters, and certain types of protein and polysaccharide polymers. The term "bioerodible" or "biodegradable", as used herein, refer to polymers that dissolve or degrade within a period that is acceptable in the desired application (usually in vivo therapy), typically less than about five years, and more preferably less than about one year, once exposed to a physiological solution of pH between about 6–8 and at a temperature of between about 25° C.–38° C.

Preferred polymers include poly(hydroxy acids), especially poly(lactic acid-co-glycolic acid) ("PLGA") that degrade by hydrolysis following exposure to the aqueous environment of the body. The polymer is then hydrolyzed to yield lactic and glycolic acid monomers, which are normal byproducts of cellular metabolism. The rate of polymer disintegration can vary from several weeks to periods of greater than one year, depending on several factors including polymer molecular weight, ratio of lactide to glycolide monomers in the polymer chain, and stereoregularity of the monomer subunits (mixtures of L and D stereoisomers disrupt the polymer crystallinity enhancing polymer breakdown). Microspheres may contain blends of two and more biodegradable polymers, of different molecular weight and/or monomer ratio.

Derivatized biodegradable polymers are also suitable for use in the present invention, including hydrophilic polymers attached to PLGA and the like. To form microspheres, in particular, a variety of techniques known in the art can be used. These include, for example, single or double emulsion steps followed by solvent removal. Solvent removal may be accomplished by extraction, evaporation or spray drying among other methods.

In the solvent extraction method, the polymer is dissolved in an organic solvent that is at least partially soluble in the extraction solvent such as water. The bioactive molecule, either in soluble form or dispersed as fine particles, is then added to the polymer solution, and the mixture is dispersed into an aqueous phase that contains a surface-active agent such as poly(vinyl alcohol). The resulting emulsion is added to a larger volume of water where the organic solvent is removed from the polymer/bioactive agent to form hardened microparticles.

In the solvent evaporation method, the polymer is dissolved in a volatile organic solvent. The bioactive molecule, either in soluble form or dispersed as fine particles, is then added to the polymer solution, and the mixture is suspended in an aqueous phase that contains a surface-active agent such as poly(vinyl alcohol). The resulting emulsion is stirred until most of the organic solvent evaporates, leaving solid microspheres.

In the spray drying method, the polymer is dissolved in a suitable solvent, such as methylene chloride (e.g., 0.04 g/ml). A known amount of bioactive molecule (drug) is then suspended (if insoluble) or co-dissolved (if soluble) in the polymer solution. The solution or the dispersion is then spray-dried. Microspheres ranging in diameter between one and ten microns can be obtained with a morphology, which depends on the selection of polymer.

Other known methods, such as phase separation and coacervation, and variations of the above, are known in the art and also may be employed in the present invention.

B. Nanoparticles

In another embodiment, the invention employs biodegradable nanoparticles for controlled release of polymer conjugated bioactive molecules, particularly for oral administration. As used herein, the term "nanoparticles" refers to particles having a diameter of preferably between about 20.0 nanometers and about 2.0 microns, typically between about 100 nanometers and 1.0 micron.

Formulation of nanoparticles can be achieved essentially as described above for microparticles, except that high speed mixing or homogenization is used to reduce the size of the polymer/bioactive agent emulsions to below about 2.0 microns, preferably below about 1.0 micron. For example, suitable techniques for making nanoparticles are described in WO 97/04747, the complete disclosure of which is incorporated by reference herein.

EXAMPLES

I. Preparation and Characterization of Formulations for Delivering Leu-enkephalin Example 1
Preparation of Polyethylene Glycol-conjugated Leu-enkephalin (PEG-leu-enkephalin)

Leu-enkephalin covalently modified with polyethylene glycol was prepared as follows: 25 mg of leu-enkephalin was dissolved in 500 μL of anhydrous DMSO containing 50 μL TEA. 250 mg of mPEG(5000)-SPA was dissolved in 1.5 mL anhydrous DMSO and added by direct injection to the peptide solution. The reaction was allowed to proceed for 2 hours at room temperature or until >90% of the peptide was converted to its PEG-modified form. Isolation of the product, mPEG(5000)-leu-enkephalin, from reactants was accomplished by recrystallization (2x) from EtOH. The reaction product was a white solid that was >95% pegylated (as assessed by RP-HPLC).

Example 2
Preparation and Characterization of Conventional ($w_1/o/w_2$) Microparticles Containing Leu-enkephalin Conventional $w_1/o/w_2$ microparticles containing leu-enkephalin were prepared as follows: Leu-enkephalin was dissolved in a 1:9 DMSO:PBS mixture to a final concentration of 35 mg/mL (its maximum solubility in PBS). PLGA (50:50 lactide:glycolide; acid end group; inherent viscosity 0.16 L/g) was dissolved in methylene chloride to a final concentration of 200 mg/mL. The primary (w/o) emulsion was created by homogenizing 200 μL of the peptide solution with 3 mL of the polymer solution at 10,000 rpm for 3 minutes. This primary emulsion was poured into 100 mL of 0.5% PVA solution and stirred at a 750 rpm for 3–6 hours. After the solvent had evaporated and the microparticles had hardened, they were collected by filtration and dried in vacuo before analysis. The particles were characterized for core loading (CL), encapsulation efficiency (EE), particle size (PS), and initial release (IR) of their contents as follows. Table 1 shows the results.

Core loading measurement of the microspheres was done by dissolving 10 mg of microspheres in 50% acetonitrile followed by centrifugation to pellet the insoluble polymer. Aliquots were analyzed by RP-HPLC and compared to representative standards prepared in 50% acetonitrile. Initial release of contents from microspheres was measured by suspending 20 mg samples in 2 mL of PBS (50 mM, pH 7.2) containing 0.02% Tween 20 and 25% EtOH. The suspensions were vortexed and incubated at 37° C. After 1 hour, aliquots were removed, filtered and analyzed for the amount released by RP-HPLC. This accelerated release at 1 hour was shown to correlate well with the amount of active released after 1 day in PBS without EtOH.

Example 3
Preparation and Characterization of Conventional ($w_1/o/w_2$) Microparticles Containing PEG-leu-enkephalin Conjugate Conventional $w_1/o/w_2$ microparticles containing PEG-leu-enkephalin were prepared as follows: PEG-leu-enkephalin was dissolved in a 1:9 DMSO:PBS mixture to a final concentration of 50 mg/mL. PLGA (50:50 lactide:glycolide; acid end group; inherent viscosity 0.16 L/g) was dissolved in methylene chloride to a final concentration of 200 mg/mL. The primary (w/o) emulsion was created by homogenizing 200 μL of the peptide solution with 3 mL of the polymer solution at 10,000 rpm for 3 minutes. This primary emulsion was poured into 100 mL of 0.5% PVA solution and allowed to stir at a 750 rpm for 3–6 hours. After the solvent had evaporated and the microparticles had hardened, they were collected by filtration and dried in vacuo before analysis. The particles were characterized for core loading (CL), encapsulation efficiency (EE), particle size (PS), and initial release (IR) of their contents as described in Example 2. These data are presented in Table 1.

Example 4
Preparation and Characterization of Monophase Microparticles Containing Leu-enkephalin Monophase microparticles containing unmodified leu-enkephalin were prepared as follows: 10 mg of leu-enkephalin was dissolved in 1 mL methylene chloride containing 30 μL TFA. 90 mg of PLGA (50:50 lactide:glycolide; lauryl end group; inherent viscosity 0.61 L/g) was then dissolved in the organic peptide solution. The primary (o/w) emulsion was formed by vortexing this solution with 2.5 mL of 2.5% PVA for 3 minutes. Forced air (15 minutes) and stirring (6–8 hours) were used to evaporate the solvent and harden the microparticles. After hardening, the microparticles were collected by filtration and dried in vacuo before analysis. Data for core loading (CL), encapsulation efficiency (EE), particle size (PS), and initial release (IR) of contents are presented in Table 1.

Example 5
Preparation and Characterization of Monophase Microparticles Containing PEG-leu-enkephalin Conjugate Monophase microparticles containing PEG-leu-enkephalin were prepared as follows: 50 mg PEG-leu-enkephalin and 150 mg PLGA (50:50 lactide:glycolide; lauryl end group; inherent viscosity 0.61 L/g) were dissolved in 2 mL methylene chloride. The primary (o/w) emulsion was formed by vortexing the organic peptide/polymer solution with 5 mL of 2.5% PVA for 3 minutes. The organic solvent was removed from the microparticles by stirring/vacuum evaporation for 2 hours. After microparticles hardened, they were collected by filtration and dried in vacuo before analysis. Data for core loading (CL), encapsulation efficiency (EE), particle size (PS), and initial release (IR) of contents are presented in Table 1.

Example 6
Increased Drug Loading for Pegylated Leu-enkephalin

Data from Table 1 shows that covalent coupling of PEG 5000 to leu-enkephalin increases the drug loading (CL) attainable from 0.07% to 0.36% for the double emulsion technique and from 0.3% to 3.95% for the monophase method. Pegylation also resulted in greatly improved encapsulation efficiency for the two methods. The initial release ("burst") was slightly less (better) for the pegylated than for unpegylated peptides made by the monophase, and the drug core load was more than 10 times greater for the pegylated peptide. The higher drug coreload allows smaller doses of biodegradable drug delivery systems to be administered to patients to achieve the desired drug dose.

TABLE 1

Characteristics of Leu-Enkephalin and PEG-Leu-Enkephalin Microparticles.

| | Leu-enkephalin | | PEG-Leu-enkephalin | |
|---|---|---|---|---|
| | Double-emulsion | Monophase | Double-emulsion | Monophase |
| TL (%)[a] | 1.64 | 10 | 1.64 | 10 |
| CL (%) | 0.07 | 0.3 | 0.36 | 3.95 |
| EE (%) | 4.43 | 3.04 | 17 | 40.3 |
| PS ($\mu$m) | 50–250 | 20–100 | 50–200 | 40–100 |
| IR (%) | 47.1 | 22.5 | ND | 20.8 |

Theoretical loading (weight of active/total weight of active and polymer)
CL—Coreload (wt % of active in microparticle as isolated)
EE—Encapsulation Efficiency (% of active encapsulated in process)
PS—Mean Particle Size (estimated from SEM)
IR—Initial Release at 1 h from in vitro dissolution in PBS (50 mM, pH 7.2) containing 0.02% Tween 20 and 25% EtOH at 37° C.
ND—Not detectable

II. Preparation, Characterization and Administration of Formulations for Delivering Biphalin

Example 7
Increased Drug Loading and Decreased Burst for Pegylated Biphalin

Biphalin is a synthetic peptide with analgesic activity in mammals. With two PEG 2000 chains attached it has a longer duration of analgesic action after intravenous administration than does the unpegylated peptide. Biphalin and pegylated biphalin were compared for their behavior in PLGA microsphere encapsulation as described in the Examples below. As shown in Table 2, pegylated biphalin has a higher drug core loading, higher encapsulation efficiency, and lower initial release level (burst) than the unpegylated peptide.

Example 8
Preparation and Characterization of Conventional ($w_1/o/w_2$) Microparticles Containing Biphalin Conventional $w_1/o/w_2$ microparticles containing PEG-biphalin were prepared as follows: Biphalin was dissolved in a ternary PBS:DMSO:acetic acid (5:1:1.5) mixture to a final concentration of 35 mg/mL. PLGA (50:50 lactide:glycolide; acid end group; inherent viscosity 0.16 L/g) was dissolved in methylene chloride to a final concentration of 200 mg/mL. The primary (w/o) emulsion was created by homogenizing 200 $\mu$L of the peptide solution with 3 mL of the polymer solution at 10,000 rpm for 3 minutes. This primary emulsion was poured into 100 mL of 0.5% PVA solution and allowed to stir at 750 rpm for 3 hours. After the solvent had evaporated and the microparticles had hardened, they were washed with water, collected by filtration and dried in vacuo before analysis. Data for core loading (CL), encapsulation efficiency (EE), particle size (PS), and initial release (IR) of contents are shown in Table 2.

Example 9
Preparation and Characterization of Conventional ($w_1/o/w_2$) Microparticles Containing PEG-biphalin Conjugate Conventional $w_1/o/w_2$ microparticles containing PEG-biphalin were prepared as follows: PEG-biphalin was dissolved in PBS to a final concentration of 50 mg/mL. PLGA (50:50 lactide:glycolide; acid end group; inherent viscosity 0.16 L/g) was dissolved in methylene chloride to a final concentration of 200 mg/mL. The primary (w/o) emulsion was created by homogenizing 200 $\mu$L of the peptide solution with 3 mL of the polymer solution at 10,000 rpm for 3 minutes. This primary emulsion was poured into 100 mL of 0.5% PVA solution and allowed to stir at a 750 rpm for 3 hours. After the solvent had evaporated and the microparticles had hardened, they were washed with water, collected by filtration and dried in vacuo before analysis. Data for core loading (CL), encapsulation efficiency (EE), particle size (PS), and initial release (IR) of contents are presented in Table 2.

Example 10
Preparation and Characterization of Monophase Microparticles Containing Biphalin Monophase microparticles containing unmodified biphalin were prepared as follows: 20 mg of biphalin and 180 mg of PLGA (50:50 lactide:glycolide; lauryl end group; inherent viscosity 0.61 L/g) were dissolved in 2 mL of a 1:3 acetic acid:methylene chloride mixture. The primary emulsion was created by vortexing the oil phase with 5 mL of 1% PVA for 3 minutes. Removal of the organic solvents from the primary o/w emulsion was accomplished by vacuum evaporation under stirring for 4 hours. After solvent removal, the hardened microparticles were collected by filtration and washed several times with distilled-deionized water to remove any nonspecifically bound PVA or biphalin. Finally, the microparticles were dried in vacuo before analysis. Data for core loading (CL), encapsulation efficiency (EE), particle size (PS), and initial release (IR) of contents are shown in Table 2.

Example 11
Preparation and Characterization of Monophase Microparticles Containing PEG-biphalin Conjugate Monophase microparticles containing PEG-biphalin were prepared as follows: 180 mg of PLGA (50:50 lactide:glycolide; lauryl end group; inherent viscosity 0.61 L/g) and 20 mg of PEG-biphalin were dissolved in 2 mL methylene chloride. The primary emulsion was created by vortexing the polymer/peptide solution with 5 mL of 2.5% polyvinyl alcohol (PVA, 80–85% hydrolyzed) for 3 minutes. The organic solvent was removed from the primary emulsion (o/w) by vacuum evaporation under stirring for 4 hours. The hardened microparticles were collected by filtration and washed several times with distilled water to remove any nonspecifically bound PVA or PEG-biphalin. Finally, the microparticles were dried in vacuo before analysis. Data for core loading (CL), encapsulation efficiency (EE), particle size (PS), and initial release (IR) of contents are presented in Table 2.

Example 12
Analgesic Effect on a Mammal Following Administration of Pegylated Biphalin in a Biodegradable Microsphere To evaluate the improved delivery in vivo of biphalin administered according to the present invention, a comparison study can be performed as follows: Pegylated biphalin PLGA microspheres can be prepared by the double emulsion method as described in Example 9. The microspheres are suspended in a medium of carboxymethylacellulose (0.5%) in water with 0.5% Tween-20. An effective dose is then administered subcutaneously to Sprague-Dawley rats and the analgesic effect is measured by, for example, the tail-flick assay. The microsphere-encapsulated PEG-biphalin has an analgesic effect which last longer than that for an unencapsulated PEG-biphalin control injection. The experiment can be repeated with PLGA-encapsulated PEG-biphalin prepared by the monophase method of Example 11 with similar results.

TABLE 2

Characteristics of Biphalin and PEG-Biphalin Microparticles

| | Biphalin | | PEG-Biphalin | |
|---|---|---|---|---|
| | Double-emulsion | Monophase | Double-emulsion | Monophase |
| TL (%)[a] | 1.0 | 10 | 1.64 | 10 |
| CL (%) | 0.24 | 0.36 | 1.48 | 6.86 |
| EE (%) | 14.28 | 3.64 | 90.52 | 68.6 |
| PS ($\mu$m) | 50–250 | 20–100 | 20–200 | 20–100 |
| IR (%) | ND | 49.4 | 19 | 15.6 |

[a]Theoretical loading (weight of active/total weight of active and polymer)
CL—Coreload (wt % of active in microparticle as isolated)
EE—Encapsulation Efficiency (% of active encapsulated in process)
PS—Mean Particle Size (estimated from SEM)
IR—Initial Release at 1 h from in vitro dissolution in PBS (50 mM, pH 7.2) containing 0.02% Tween 20 and 25% EtOH at 37° C.
ND—Not detectable III. Preparation, Characterization and Administration of Formulations for Delivering Insulin Example 13
Preparation of Polyethylene Glycol-conjugated Human Insulin (PEG-insulin)

Human insulin was covalently modified with polyethylene glycol as follows: 116 mg of recombinant human insulin was dissolved in 4 mL anhydrous DMSO containing 200 $\mu$L TEA. 1 g of mPEG(5000)-SPA was dissolved in 10 mL anhydrous DMSO and added to the insulin solution by direct injection. The reaction proceeded overnight (6–10 hours) at room temperature or until >90% of the protein was pegylated. The unreacted PEG and pegylated insulin were isolated by precipitation (2x) from $Et_2O$. The final product was a white granular solid that was >95% pegylated (according to RP-HPLC analysis).

Example 14
Preparation and Characterization of Conventional ($w_1/o/w_2$) Microparticles Containing Human Insulin Conventional $w_1/o/w_2$ microparticles containing human insulin were prepared as follows: recombinant human insulin was dissolved in DMSO:0.1N HCl (1:1) to a final concentration of 50 mg/mL and PLGA (50:50 lactide:glycolide; lauryl end group; inherent viscosity 0.61 L/g) was dissolved in methylene chloride to a final concentration of 200 mg/mL. The primary (w/o) emulsion was formed by homogenization of 200 $\mu$L of the protein solution and 3 mL of the polymer solution at 10,000 rpm for 3 minutes. This primary emulsion was then added to 100 mL of 0.5% PVA and allowed to stir under vacuum for 3–6 hours. Once the organic solvents were removed, the microparticles were filtered, washed several times with water, and dried in vacuo before analysis. Table 3 lists characteristics of the microparticles.

Example 15
Preparation and Characterization of Conventional ($w_1/o/w_2$) Microparticles Containing PEG-insulin Conjugate Conventional $w_1/o/w_2$ microparticles containing PEG-insulin were prepared as follows: PEG-insulin was dissolved in a DMSO:$H_2O$ (1:2) mixture to a final concentration of 50 mg/mL and PLGA (50:50 lactide:glycolide; lauryl end group; inherent viscosity 0.61 L/g) was dissolved in methylene chloride to a final concentration of 200 mg/mL. The primary (w/o) emulsion was formed by homogenization of 200 $\mu$L of the protein solution and 3 mL of the polymer solution at 10,000 rpm for 3 minutes. This primary emulsion was the added to 100 mL of 0.5% PVA and allowed to stir under vacuum for 3–6 hours. Once the organic solvents were removed, the microparticles were filtered, washed several times with water, and dried in vacuo before analysis. Table 3 lists results from analysis of the microparticles.

Example 16
Preparation and Characterization of Monophase Microparticles Containing Human Insulin Monophase microparticles containing human insulin were prepared as follows: 20 mg of recombinant human insulin ($Zn^{2+}$-insulin salt) was dissolved in 2 mL of an acetic acid:methylene chloride (1.4:1) mixture. 180 mg of PLGA (50:50 lactide:glycolide; lauryl end group; inherent viscosity 0.61 L/g) was then dissolved in the organic peptide solution. The primary emulsion was created by vortexing the organic peptide/polymer solution with 5 mL of 1% PVA for 3 minutes. The organic solvents were removed by vacuum evaporation under stirring for 2 hours. The partially hardened microparticles were added to a beaker containing 100 mL water and stirred for another 2 hours to completely remove all organic solvents. The microparticles were collected by filtration, washed several times with water and dried in vacuo before analysis. Table 3 lists results from analysis of the microparticles.

Example 17
Preparation and Characterization of Monophase Microparticles Containing PEG-insulin Conjugate Monophase microparticles containing PEG-insulin were prepared as follows: 63 mg of PEG-insulin and 137 mg of PLGA (50:50 lactide:glycolide; lauryl end group; inherent viscosity 0.61 L/g) were dissolved in 2 mL of methylene chloride. The primary emulsion was formed by vortexing the oil phase with 5 mL of 1% PVA for 3 minutes. Solvent removal was accomplished by vacuum evaporation for 2 h followed by stirring under ambient conditions for 1 hour.

The hardened microparticles were collected by filtration and washed several times with water before drying in vacuo and analyzing. Table 3 lists results from analysis of the microparticles.

Example 18
Increased Drug Loading and Encapsulation Efficiency for Pegylated Insulin Data in Table 3 show that pegylated insulin achieves increased drug loading in PLGA microspheres prepared by both the monophase and double emulsion methods. Pegylated insulin also has higher encapsulation efficiency, a major advantage when high value biologically active peptides and proteins are used.

TABLE 3

Characteristics of Insulin and PEG-Insulin Microparticles.

|  | Insulin | | PEG-Insulin | |
| --- | --- | --- | --- | --- |
|  | Double-emulsion | Monophase | Double-emulsion | Monophase |
| TL (%)[a] | 1.64 | 10 | 1.64 | 31.5 |
| CL (%) | 0.23 | 0.6 | 0.54 | 15.5 |
| EE (%) | 13.86 | 6 | 33 | 49.2 |
| PS ($\mu$m) | 100–350 | 30–100 | 50–250 | 50–100 |

[a]Theoretical loading (weight of active/total weight of active and polymer)
CL—Coreload (wt % of active in microparticle as isolated)
EE—Encapsulation Efficiency (% of active encapsulated in process)
PS—Mean Particle Size (estimated from SEM)

Example 19
Hypoglycemic Effect of PLGA-Encapsulated PEG-Insulin

PEG-Insulin PLGA microspheres and an equivalent dose of free insulin were administered subcutaneously to normal rats. Blood was drawn periodically and anticoagulated. Blood glucose levels were measured by standard tests. As shown in Table 4, use of PEG-insulin in PLGA microspheres significantly suppressed the initial reduction in blood glucose relative to the values observed for unmodified insulin. In addition, these data importantly show that the PEG-insulin microsphere preparation released its drug in a biologically active form that was able to effectively depress blood glucose levels in an in vivo animal model without the "burst" effect of unmodified, conventional formulations.

TABLE 4

In Vivo Study of Insulin and PEG-Insulin Microparticles.

|  | Insulin (Humulin-U) | | PEG-Insulin | |
| --- | --- | --- | --- | --- |
| Time (hr) | % BGL[a] | SD | % BGL[a] | SD |
| 0 | 100 | 0 | 100 | 0 |
| 1 | 25.8 | 6.6 | 111.1 | 16 |
| 2 | 14.9 | 11.4 | 86.5 | 17.6 |
| 4 | 68.1 | 11.6 | 97 | 13.3 |
| 6 | 89.3 | 7 | 98.5 | 12.1 |
| 8 | 75 | 1.7 | 82 | 6.8 |
| 12 | 75.8 | 8.2 | 88.8 | 6.6 |

[a]% BGL denotes the glucose values shown are normalized to a percentage of basal levels

IV. Preparation and Characterization of Formulations for Delivering GM-CSF

Example 20
Preparation of Polyethylene Glycol Conjugated GM-CSF

GM-CSF can be covalently conjugated to polyethylene glycol (PEG) as follows: 100 mg of GM-CSF is dissolved in 10 ml pH 7.5 phosphate buffer, at room temperature. 100 mg tresyl-monomethoxy-polyethylene glycol (MW=5000 daltons) is then added, and the mixture stirred for 1 hour. The unreacted GM-CSF and pegylated GM-CSF fractions are isolated from unreacted tresyl-monomethoxy-polyethylene glycol by gel chromatography. The pegylated GM-CSF is then dialyzed into 100 mM Tris buffer and adjusted to a concentration of 50 mg/ml.

Example 21

Preparation of Microparticles Encapsulating Pegylated GM-CSF

Microparticles encapsulating pegylated GM-CSF can be prepared as follows: 6.0 gm of PLGA (50:50 lactide:glycolide; inherent viscosity 0.35 l/g) is dissolved in 20 ml ethyl acetate. 1 ml of pegylated GM-CSF from Example 20 is added and stirred rapidly with a homogenizer at 10,000 rpm to create a water-in-oil emulsion. The polymer/drug/ethyl acetate emulsion is then pumped through a static mixer in combination with a pumped stream of water containing 1% polyvinyl alcohol (PVA). This action produces a w/o/w emulsion, which was subsequently added to 1 liter of 5C water with stirring. After 2 hours the hardened PLGA microspheres containing pegylated GM-CSF are collected on a 25 micron sieve and dried. The resulting microspheres will be in a size range of between 25–200 μm.

Example 22

Preparation of Nanoparticles Encapsulating Pegylated GM-CSF

Nanoparticles encapsulating pegylated GM-CSF can be prepared as follows: 3.0 gm of PLGA (material same as in Example 21) is dissolved in 5 ml dichloromethane and 5 ml acetone. 0.5 ml of pegylated GM-CSF from Example 20 is added and the mixture stirred at 10,000 rpm with a homogenizer. The mixture is added to 200 ml water containing 5% PVA. The mixture is then homogenized at 15,000 rpm for such time as is required to form nanoparticles of less than about 1.0 micron in diameter. The organic solvents can be removed by vacuum and the nanospheres can be recovered from the water and dried.

Equivalents

Those skilled in the art will recognize, or be able to ascertain using no more than routine experimentation, many equivalents of the specific embodiments of the invention described herein. Such equivalents are intended to be encompassed by the following claims. In addition, the entire contents of all patents and publications cited herein is hereby incorporated by reference.

What is claimed is:

1. A pharmaceutical formulation for controlled release of a bioactive molecule, the formulation comprising a biodegradable polymer in combination with a conjugate of a bioactive molecule and a hydrophilic polymer, wherein the formulation is in the form of microparticles or nanoparticles encapsulating the conjugate, the formulation having a lower initial burst than a formulation of the bioactive molecule without being conjugated to the hydrophilic polymer.

2. The pharmaceutical formulation of claim 1 wherein the bioactive molecule and the hydrophilic polymer are covalently conjugated.

3. The pharmaceutical formulation of claim 1 wherein the biodegradable polymer is selected from the group consisting of polyhydroxy acids, polylactic acids, polyglycolic acids, and copolymers thereof.

4. The pharmaceutical formulation of claim 3 wherein the biodegradable polymer is selected from the group consisting of polyanhydrides, polyorthoesters, and polysaccharide polymers.

5. The pharmaceutical formulation of claim 1 wherein the hydrophilic polymer is selected from the group consisting of polyethylene glycol, polypropylene glycol, copolymers of polyethylene glycol and polypropylene glycol, and linear and branched derivatives of polyethylene glycol and polyethylene glycol/polypropylene glycol copolymers.

6. The pharmaceutical formulation of claim 1 wherein said bioactive molecule is selected from the group consisting of α-interferon, β-interferon. γ-interferon, erythropoietins, granulocyte colony stimulating factor, granulocyte macrophage colony stimulating factor, interleukin 1, interleukin 2, interleukin 3, interleukin 12, asparaginase, adenosine deaminase, insulin, glucagon-like peptides, ACTH, glucagon, somatostatin, somatostatin, rhymosin, parathyroid hormone, pigmentary hormones, somatomedin, leuteinizing hormone, chorionic gonadotropin, hypothalmic releasing factors, antidiuretic hormones, thyroid stimulating hormone, endorphins, enkephalins, biphalin, prolactin, monoclonal antibodies, polyclonal antibodies, antisense oligonucleotides, aptamers, therapeutic genes, heparin, low molecular weight heparin and small bioactive molecules.

7. A method for controlled systemic delivery of bioactive molecules to a subject comprising administering to the subject a formulation comprising a biodegradable polymer in combination with a conjugate of a bioactive molecule and a hydrophilic polymer, wherein the formulation is in the form of microparticles or nanoparticles encapsulating the conjugate, the formulation having a lower initial burst than a formulation of the bioactive molecule without being conjugated to the hydrophilic polymer.

8. The method of claim 7 wherein the composition is administered orally.

9. The method of claim 7 wherein the composition is administered by inhalation or mucosal delivery.

10. The method of claim 7 wherein the composition is administered by injection.

11. The method of claim 10 wherein the injection is subcutaneous or intramuscular.

12. The method of claim 7 wherein the bioactive molecule and the hydrophilic polymer are covalently conjugated.

13. The method of claim 7 wherein the biodegradable polymer is selected from the group consisting of polyhydroxy acids, polylactic acids, polyglycolic acids, and copolymers thereof.

14. The method of claim 7, wherein the hydrophilic polymer is selected from the group consisting of polyethylene glycol, polypropylene glycol, copolymers of polyethylene glycol and polypropylene glycol, and linear and branched derivatives of polyethylene glycol and polyethylene glycol/polypropylene glycol copolymers.

15. The method of claim 7 wherein said bioactive molecule is selected from the group consisting of α-interferon, β-interferon, γ-interferon, erythropoietins, granulocyte colony stimulating factor, granulocyte macrophage colony stimulating factor, interleukin 1, interleukin 2, interleukin 3, interleukin 12, asparaginase, adenosine deaminase, insulin, glucagon-like peptides, ACTH, glucagon, somatostatin, somatotropin, thymosin, parathyroid hormone, pigmentary hormones, somatomedin, leuteinizing hormone, chorionic gonadotropin, hypothalmic releasing factors, antidiuretic hormones, thyroid stimulating hormone, endorphins, enkephalins, biphalin, prolactin, monoclonal antibodies, polyclonal antibodies, antisense oligonucleotides, aptamers, therapeutic genes, heparin, low molecular weight heparin and small bioactive molecules.

16. A method for increasing bioavailability of a bioactive molecule, comprising conjugating the bioactive molecule with a hydrophilic polymer, formulating the conjugated bioactive molecule with a biodegradable polymer, wherein the biodegradable polymer is in the form of microparticles or nanoparticles encapsulating the conjugated bioactive molecule, and administering the resulting formulation to a subject, the formulation having a lower initial burst than a formulation of the bioactive molecule without being conjugated to the hydrophilic polymer.

17. The method of claim 16 wherein the formulation is administered orally.

18. The method of claim 16 wherein the bioactive molecule and the hydrophilic polymer are covalently conjugated.

19. The method of claim 16 wherein the biodegradable polymer is selected from the group consisting of polyhydroxy acids, polylactic acids, polyglycolic acids, and copolymers thereof.

20. The method of claim 16 wherein the hydrophilic polymer is selected from the group consisting of polyethylene glycol, polypropylene glycol, copolymers of polyethylene glycol and polypropylene glycol, and linear and branched derivatives of polyethylene glycol and polyethylene glycol/polypropylene glycol copolymers.

21. The method of claim 16, wherein said bioactive molecule is selected from the group consisting of α-interferon, β-interferon, γ-interferon, erythropoietins, granulocyte colony stimulating factor, granulocyte macrophage colony stimulating factor, interleukin 1, interleukin 2, interleukin 3, interleukin 12, asparaginase, adenosine deaminase, insulin, glucagon-like peptides, ACTH, glucagon, somatostatin, somatotropin, thymosin, parathyroid hormone, pigmentary hormones, somatomedin, leuteinizing hormone, chorionic gonadotropin, hypothalmic releasing factors, antidiuretic hormones, thyroid stimulating hormone, endorphins, enkephalins, biphalin, prolactin, monoclonal antibodies, polyclonal antibodies, antisense oligonucleotides, aptamers, therapeutic genes, heparin, low molecular weight heparin and small bioactive molecules.

22. A method for reducing immunogenicity of a bioactive molecule, comprising conjugating the bioactive molecule with a hydrophilic polymer, formulating the conjugated bioactive molecule with a biodegradable polymer, and administering the resulting formulation to a subject, wherein the formulation is in the form of microparticles or nanoparticles encapsulating the conjugate, the formulation having a lower initial burst than a formulation of the bioactive molecule without being conjugated to the hydrophilic polymer.

23. The method of claim 22 wherein the formulation is administered orally.

24. The method of claim 22 wherein the bioactive molecule and the hydrophilic polymer are covalently conjugated.

25. The method of claim 22 wherein the biodegradable polymer is selected from the group consisting of polyhydroxy acids, polylactic acids, polyglycolic acids, and copolymers thereof.

26. The method of claim 22 wherein the hydrophilic polymer is selected from the group consisting of polyethylene glycol, polypropylene glycol, copolymers of polyethylene glycol and polypropylene glycol, and linear and branched derivatives of polyethylene glycol or polyethylene glycol/polypropylene glycol copolymers.

27. The method of claim 22, wherein said bioactive molecule is selected from the group consisting of α-interferon, β-interferon, γ-interferon, erythropoietins, granulocyte colony stimulating factor, granulocyte macrophage colony stimulating factor, interleukin 1, interleukin 2, interleukin 3, interleukin, 12, asparaginase, adenosine deaminase, insulin, glucagon-like peptides, ACTH, glucagon, somatostatin, somatotropin, thymosin, parathyroid hormone, pigmentary hormones, somatomedin, leuteinizing hormone, chorionic gonadotropin, hypothalmic releasing factors, antidiuretic hormones, thyroid stimulating hormone, endorphins, enkephalins, biphalin, prolactin, monoclonal antibodies, polyclonal antibodies, antisense oligonucleotides, aptamers, therapeutic genes, heparin, low molecular weight heparin and small bioactive molecules.

28. A method for producing a pharmaceutical formulation for controlled release of a bioactive molecule, the method comprising:

dissolving (a) a biodegradable polymer and (b) a conjugate of a bioactive molecule and a hydrophilic polymer in a solvent to form a monophase, and forming microparticles or nanoparticles comprising the biodegradable polymer encapsulating the conjugate.

29. The formulation of claim 1, wherein the biodegradable polymer comprises a copolymer of polylactic acid and polyglycolic acid and the hydrophilic polymer comprises polyethylene glycol.

30. The formulation of claim 1, wherein the bioactive molecule is selected from the group consisting of a protein, a peptide and a small molecule.

31. The formulation of claim 1, wherein the bioactive molecule comprises insulin.

32. A pharmaceutical formulation for controlled release of a bioactive molecule, the formulation comprising a biodegradable polymer in combination with a conjugate of a bioactive molecule and a hydrophilic polymer, wherein the biodegradable polymer comprises a derivatized biodegradable polymer containing hydrophilic and hydrophobic regions.

33. The formulation of claim 32, wherein the hydrophilic region comprises polyethylene glycol.

34. The formulation of claim 32, wherein the bioactive molecule comprises insulin.

35. The formulation of claim 32, wherein die hydrophobic region comprises a polymer selected from the group consisting of polyhydroxy acids, polylactic acids, polyglycolic acids, and copolymers thereof.

36. The formulation of claim 1, wherein the hydrophilic polymer comprises polyethylene glycol.

37. A pharmaceutical formulation for controlled release of a bioactive molecule, the formulation comprising a biodegradable polymer in combination with a conjugate of a bioactive molecule and a hydrophilic polymer, wherein the conjugate of the hydrophilic polymer and a bioactive agent is predominantly a single species.

38. The formulation of claim 37, wherein the hydrophilic polymer comprises polyethylene glycol.

39. The formulation of claim 38, wherein the polyethylene glycol is linked to the bioactive molecule predominantly at a single site on the bioactive molecule.

* * * * *